US010520487B2

(12) United States Patent
Koo et al.

(10) Patent No.: US 10,520,487 B2
(45) Date of Patent: Dec. 31, 2019

(54) ELECTRIC-FIELD IMAGER FOR ASSAYS

(71) Applicant: Maxim Integrated Products, Inc., San Jose, CA (US)

(72) Inventors: Ronald B. Koo, Los Altos, CA (US); Henry Grage, Johns Creek, GA (US)

(73) Assignee: Maxim Integrated Products, Inc., San Jose, CA (US)

( * ) Notice: Subject to any disclaimer, the term of this patent is extended or adjusted under 35 U.S.C. 154(b) by 20 days.

(21) Appl. No.: 15/956,299

(22) Filed: Apr. 18, 2018

(65) Prior Publication Data

US 2018/0238857 A1 Aug. 23, 2018

Related U.S. Application Data

(63) Continuation of application No. 14/859,943, filed on Sep. 21, 2015, now Pat. No. 10,107,790.

(60) Provisional application No. 62/156,954, filed on May 5, 2015.

(51) Int. Cl.
*G01N 33/483* (2006.01)
*G01N 27/12* (2006.01)
*G01N 27/04* (2006.01)
*G06T 7/00* (2017.01)
*G01N 15/10* (2006.01)
*G01N 33/49* (2006.01)
(Continued)

(52) U.S. Cl.
CPC ..... *G01N 33/4833* (2013.01); *G01N 15/1031* (2013.01); *G01N 27/046* (2013.01); *G01N 27/122* (2013.01); *G01N 33/49* (2013.01); *G01N 33/54373* (2013.01); *G06T 7/0012* (2013.01); *G01N 2015/0092* (2013.01); *G01N 2015/1006* (2013.01); *G06T 2207/30104* (2013.01)

(58) Field of Classification Search
CPC ........ G06T 2207/30104; G06T 7/0012; G01N 27/122; G01N 27/046; G01N 33/4833
USPC .. 324/691, 600, 200, 207.13, 219, 239–247, 324/500, 529, 530, 750.08, 754.15, 76.11, 324/92; 73/152.18, 152.02
See application file for complete search history.

(56) References Cited

U.S. PATENT DOCUMENTS

2006/0261431 A1* 11/2006 Kim .................. H01L 27/14609
257/462
2010/0019155 A1* 1/2010 Klunder ................. B82Y 15/00
250/363.01
(Continued)

OTHER PUBLICATIONS

Laborde, C. et al., "Real-time imaging of microparticles and living cells with CMOS nanocapacitor arrays", Nature Nanotechnology, vol. 10, Sep. 2015, pp. 791-796.
(Continued)

*Primary Examiner* — Melissa J Koval
*Assistant Examiner* — Trung Nguyen
(74) *Attorney, Agent, or Firm* — Kevin E. West; Advent, LLP

(57) ABSTRACT

This disclosure describes an electric-field imaging system and method of use. In accordance with implementations of the electric-field imaging system, a fluid sample can be placed on top of a pixel-based impedance sensor. An image of the target analytes can be created immediately afterwards. From this image, computer imaging algorithms can determine attributes (e.g., size, type, morphology, volume, distribution, number, concentration, or motility, etc.) of the target analytes.

13 Claims, 6 Drawing Sheets

(51) Int. Cl.
  *G01N 33/543* (2006.01)
  *G01N 15/00* (2006.01)

(56) References Cited

U.S. PATENT DOCUMENTS

| | | | |
|---|---|---|---|
| 2013/0265459 A1* | 10/2013 | Duparre | H04N 5/23238 |
| | | | 348/218.1 |
| 2014/0001058 A1 | 1/2014 | Ghaffari et al. | |
| 2015/0293060 A1* | 10/2015 | Jacobsen | G01N 29/036 |
| | | | 506/12 |
| 2016/0245788 A1 | 8/2016 | Wang et al. | |
| 2017/0038282 A1 | 2/2017 | Veiseh et al. | |

OTHER PUBLICATIONS

Widdershoven, F. et al., "CMOS biosensor platform", IEEE, 978-1-4244-7419-6/10, 2010, pp. 36.1.1-36.1.4.

Wong, C. C. et al., "CMOS based High Density Micro Array Platform for Electrochemical Detection and Enumeration of Cells", in Proc. IEDM, 2013, pp. 373-376.

Non-Final Office Action dated Jul. 3, 2018, for U.S. Appl. No. 15/688,449.

\* cited by examiner

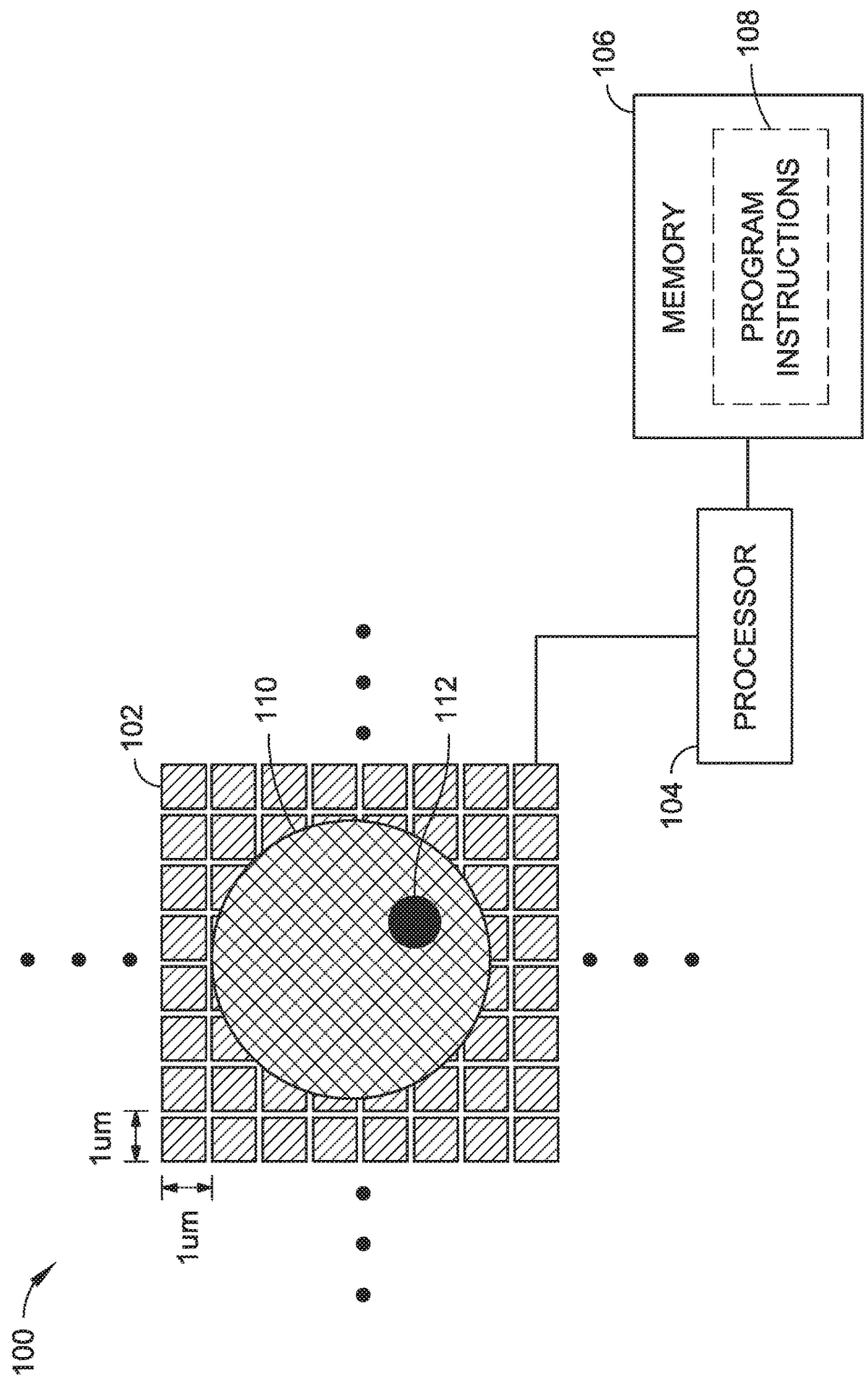

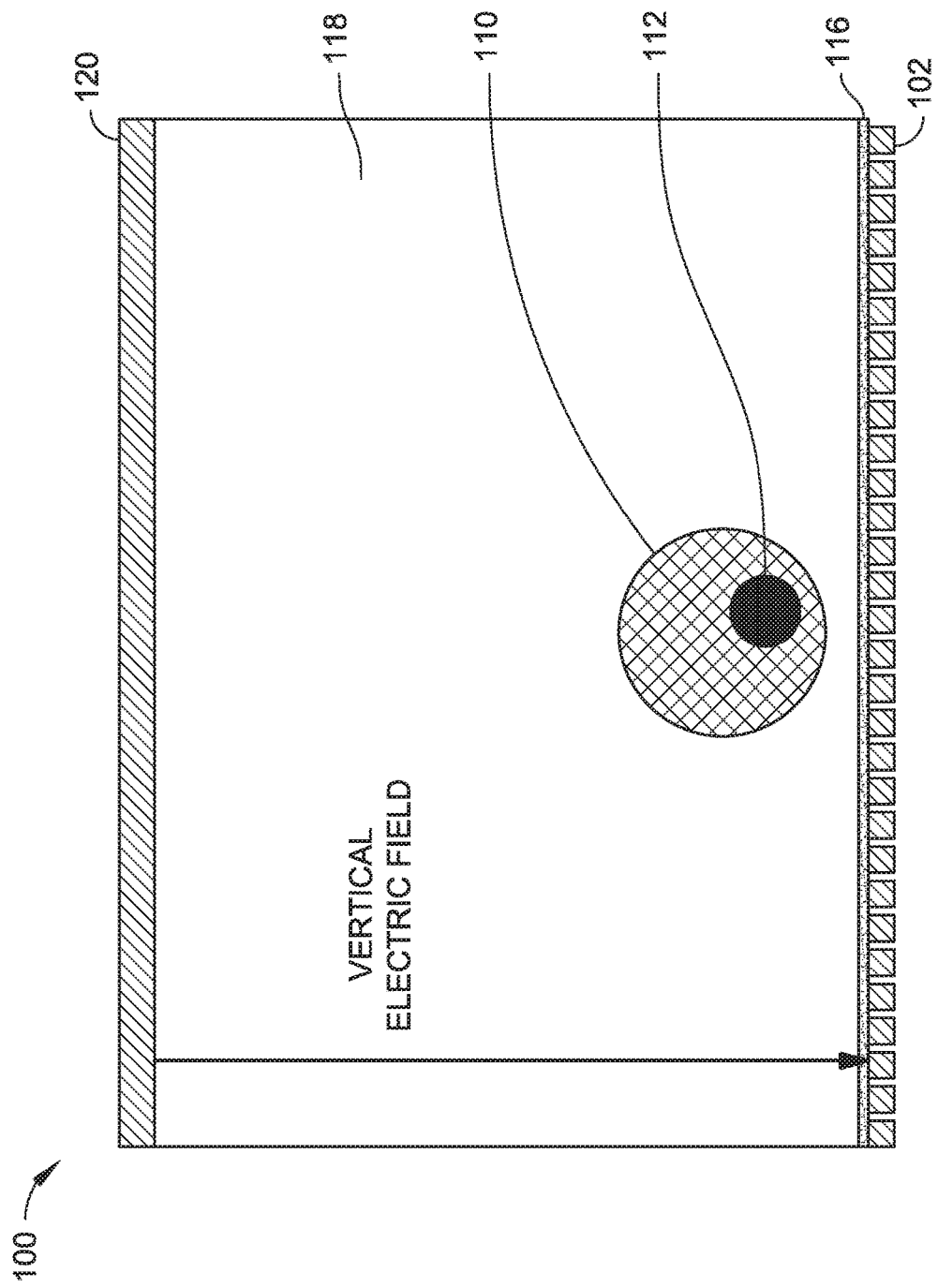

ELECTRIC-FIELD IMAGER FOR ASSAYS

CROSS-REFERENCE TO RELATED APPLICATIONS

The present application is a continuation of U.S. Non-Provisional application Ser. No. 14/859,943, filed Sep. 21, 2015, and titled "ELECTRIC-FIELD IMAGER FOR VISUALIZING CELLS." The present application claims the benefit under 35 U.S.C. § 119(e) of U.S. Provisional Application Ser. No. 62/156,954, filed May 5, 2015, and titled "ELECTRIC-FIELD IMAGER FOR VISUALIZING CELLS." U.S. Provisional Application Ser. No. 62/156,954 is and U.S. Non-Provisional application Ser. No. 14/859,943 are herein incorporated by reference in its their entirety.

BACKGROUND

Flow cytometry is the dominant method of counting red blood cells, white blood cells, and so forth. When a company is developing a flow cytometer, validation of the results from the machine is done by a human looking through a microscope and visually counting the cells on a sample smeared over a glass slide. Electric Cell-substrate Impedance Sensing (ECIS) determines how fast cells grow in a laboratory dish by measuring the impedance of the cells as they are growing. The cells block the electric field lines, and impedance increases as the cells grow and cover more and more of the sensor. Once the cells have completely covered the sensor, the impedance asymptotes.

The existing methods suffer from several limitations. For example, flow cytometer results take some time to obtain because blood samples are usually taken to a laboratory to be prepared and then run through the flow cytometer. Visual inspection to count cells is tedious for the human who has to do it and is of course prone to human error. Visual inspection results also take a considerable amount of time to obtain for the same reasons as the flow cytometer results. ECIS provides a single scalar measurement for the growth rate of a colony of cells on top of the sensor. No information is available as to how the cells cover the sensor, how many cells there are, concentration of cells, how the cells move as they grow, or the like.

SUMMARY

This disclosure describes an electric-field imaging system and method of use. In accordance with implementations of the electric-field imaging system, a fluid sample (e.g., a blood sample or other biological sample) can be placed on top of an impedance based sensor. An image of the cells can be created immediately afterwards. From this image, computer imaging algorithms can determine attributes, such as size, type, morphology, volume, distribution, number, concentration, or motility of target analytes (e.g., microparticles, viruses, cells, or labeled beads).

In some embodiments, an electric-field imaging system relies on a substantially vertical electric field. For example, if an electrode is above the electric field sensor array, then a vertical electric field can be formed between the top electrode and the sensor array. In some implementations, the metal layer of an integrated circuit can form the electric field sensor array. The sensor can have a pitch suitable for imaging red blood cells, white blood cells, platelets, or the like.

In some embodiments, an electric-field imaging system relies on a substantially horizontal electric field. For example, a single pixel, a line of pixels, or a regions of pixels can be driven, and the rest of the pixels in the electric field image sensor can receive the electric field. The presence of particles like microparticles, viruses, cells, in the fluid disturbs the electric field, resulting in a change of impedance from driving pixel to receiving pixel. Each pixel can be formed by a plate of metal.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

FIG. 1 is a schematic view of an electric-field imager implemented in accordance with an embodiment of this disclosure.

FIG. 3 is a schematic side view of an electric-field imager implemented in accordance with an embodiment of this disclosure, wherein the electric-field imager is configured to detect disturbances in a vertical electric field.

DETAILED DESCRIPTION

Overview

Figure 2A:
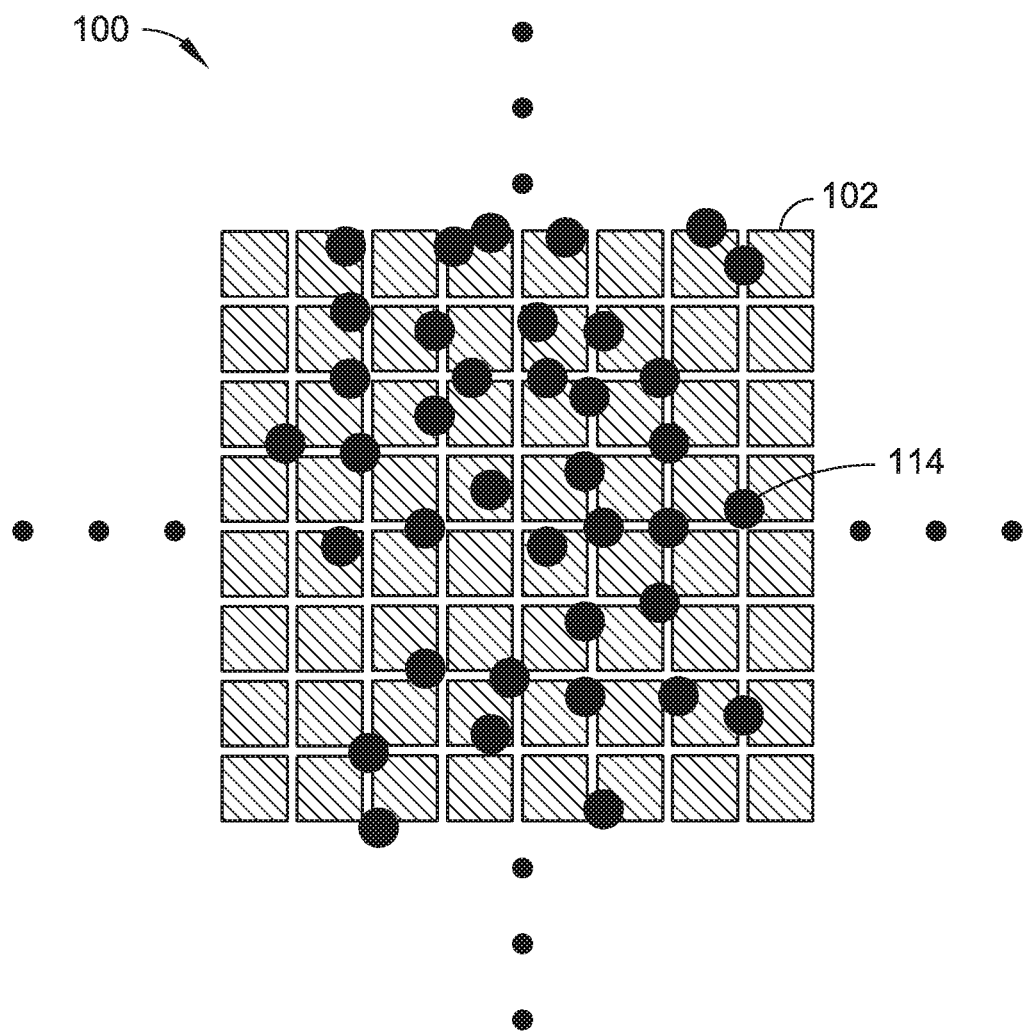
FIG. 2A illustrates an example of agglutination assaying with an electric-field imager, wherein beads covered by antibodies are dispersed.

A pixel-based image sensor is disclosed in which each pixel senses changes in the electric field above it to determine the presence of microparticles, viruses, cells, beads and also one or more attributes, such as size, type, morphology, distribution, concentration, number of microparticles, viruses, cells, beads, and so forth. In embodiments, the pitch of the pixels can vary from 10 nm to 20 um. Each pixel can be configured to measure impedance. In some embodiments, the sensor is implemented on an integrated circuit. The sensor can also be formed from patterned or printed conductors on a substrate such as glass or plastic, where at least one integrated circuit electrically connected to the conductors can be configured to measure the impedance.

Example Implementations

FIGS. 1 through 4 illustrate an electric-field imaging system 100 in accordance with various embodiments of this disclosure. Those skilled in the art will appreciate that the embodiments illustrated in the drawings and/or described herein may be fully or partially combined to result in additional embodiments. Substitutions and other modifications can also be made without departing from the scope of this disclosure. Accordingly, the illustrated and described embodiments should be understood as explanatory and not as limitations of the present disclosure.

In an embodiment illustrated in FIG. 1, an electric-field imaging system 100 is shown to include a plurality of conductive metal panels 102 making up the pixels of an active sensor area. In some implementations, the metal layer of an integrated circuit can form the electric field sensor array. The active sensor area can receive a fluid sample including target analytes (e.g., viruses, prions, sperm, cells, beads, biological microparticles, etc.), which can be deposited over the active sensor area for electric-field imaging based on changes in impedance or charge detected at respective ones of the metal panels 102. For example, FIG. 1 shows a cell 110 on the active sensor area, where the sensor pitch (e.g., panel length, width, and/or panel-to-panel separation) may be appropriate for imaging the cell 110 and various cellular structures (e.g., the cell's nucleus 112). A sensor pitch in the range of 1 um is shown in FIG. 1; however, it is noted that the sensor pitch can be larger or smaller to suit different applications. In some embodiments, the pitch is anywhere from approximately 10 nm to 20 um. To properly image individual target analytes (e.g., individual cells or microparticles of interest), the sensor pitch may be higher frequency than a Nyquist spatial sampling rate suitable for detecting a smallest member of a group of target analytes. In some implementations, detection of cellular structures or morphology can be used to distinguish between different types of biological cells (e.g., white blood cells vs. red blood cells).

The system 100 can include transmitter circuitry configured to generate drive signals that are applied to one or more of the metal panels 102 or applied to a driving electrode positioned relative to the panels 102 (e.g., as shown in FIG. 3). In some embodiments, the transmitter can include a frequency generator that feeds into one or more digital to analog converters (DACs) to generate one or more drive signals. The system 100 can also include receiver circuitry coupled to the metal panels 102, and configured to sense changes in impedance or charge detected by the metal panels 102. In some embodiments, the receiver can include one or more analog to digital converters (ADCs) configured to receive an impedance, voltage, or current reading from each of the metal panels 102 to sense changes in impedance or charge, which can result from the presence of target analytes in proximity of one or more of the metal panels 102. In some embodiments, the receiver circuitry can also include a frontend filter (e.g., low pass filter) configured to remove noise or signal components attributable to the fluid containing the target analytes, drive signal artifacts, and so forth.

The system 100 may further include processing logic embodied by a programmable logic device, a controller/microcontroller, a single or multiple core processor, an ASIC, or the like. For example, the system 100 can include a processor 104 coupled to a memory 106 (e.g., solid-state disk, hard disk drive, flash memory, etc.), where the memory includes program instructions 108, such as one or more software modules executable by the processor 104. In some embodiments, the processing logic can control transmission and receipt of signals to and from the metal panels 102. For example, the processing logic may be coupled with receiver and/or transmitter circuitry. The processing logic may be configured to generate an image based on electrical signals associated with changes in impedance or charge detected at one or more of the metal panels 102. In some embodiments, the processing logic can include fast Fourier transform (FFT) and impedance sense algorithms. The processing logic can further include one or more computer imaging software modules executable by a processor/controller to identify attributes of target analytes in the generated electric-field image. For example, the computer imaging modules may cause the processor/controller to perform a comparison between one or more portions of the generated electric-field image and a library with stored images or data associated with one or more attributes, such as size, type, morphology, distribution, concentration, number of cells/microparticles, and so forth.

In some embodiments, the system 100 can include multiple-sensor areas or regions with different sensor pitches/dimensions for targeting smaller particles (e.g., microparticles) vs. larger particles (e.g., cells). For example, a first area with larger sensor pitch can be used to image cells or larger particles. This can be useful in cases where smaller particles are not of interest and/or cases where speed is more important than resolution. On the other hand, a second area with finer sensor pitch can be used to collect higher resolution electric-field images and detect microparticles and/or resolve cellular structures. At finer resolutions, both large and small particles may be detected.

Figure 2B:
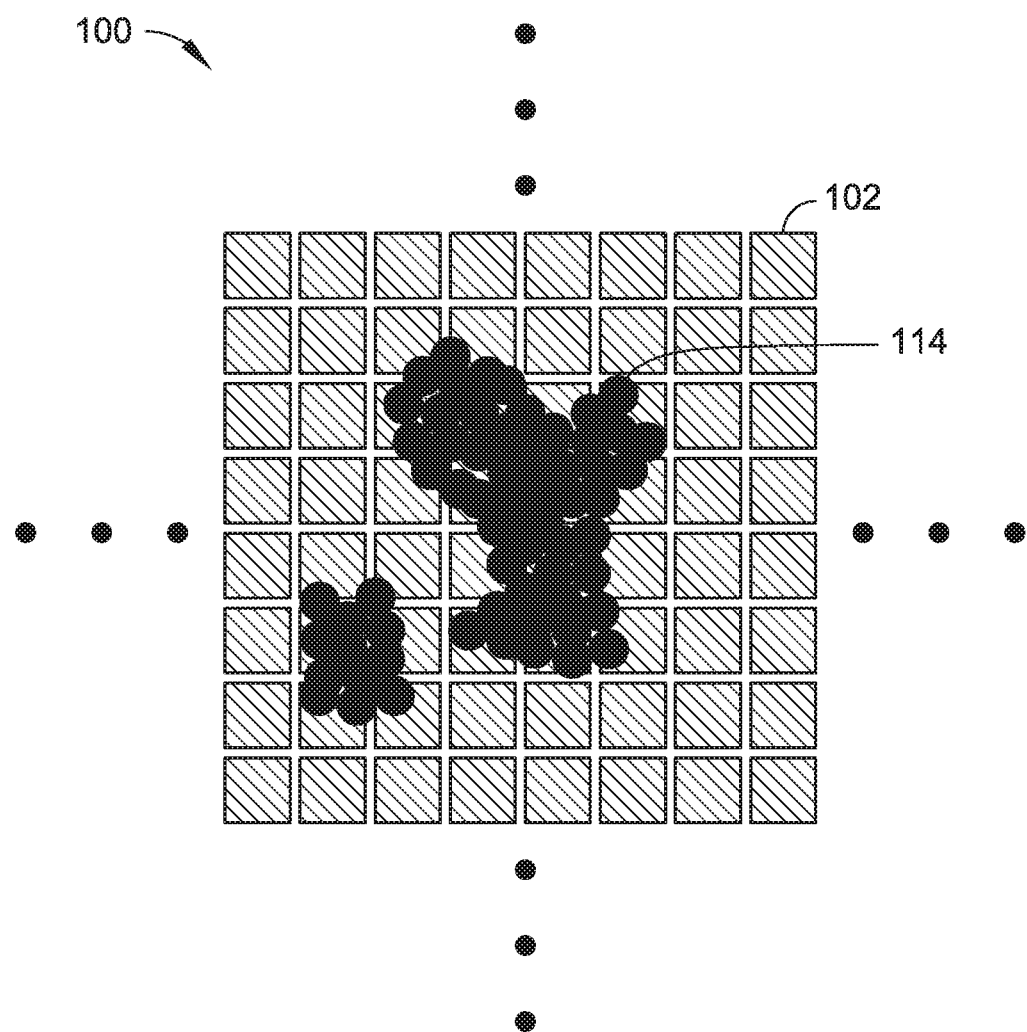
FIG. 2B illustrates an example of agglutination assaying with an electric-field imager, wherein beads covered by antibodies are agglutinated.

In some embodiments, the system 100 can be configured to collect multiple electric-field images taken at different times (e.g., time lapsed images) to monitor growth or movement of cells/microparticles. For example, time lapsed images can be used to monitor cells as they multiply or for agglutination assaying to monitor movement of dispersed particles (e.g., antibody-coated microbeads 114 shown in FIG. 2A) as they agglutinate in the presence of an antigen (e.g., as shown in FIG. 2B).

In embodiments, the system can further include a thermal sensor configured to detect a temperature of the fluid sample containing the biological cells or microparticles and/or a conductivity sensor configured to detect a conductivity of the fluid sample or portions thereof. In some implementations, the impedance-based sensor itself (e.g., one or more of the metal panels 102) can be configured to detect the conductivity of the fluid sample or sample conductivity at different regions of the active sensor area.

Figure 4:
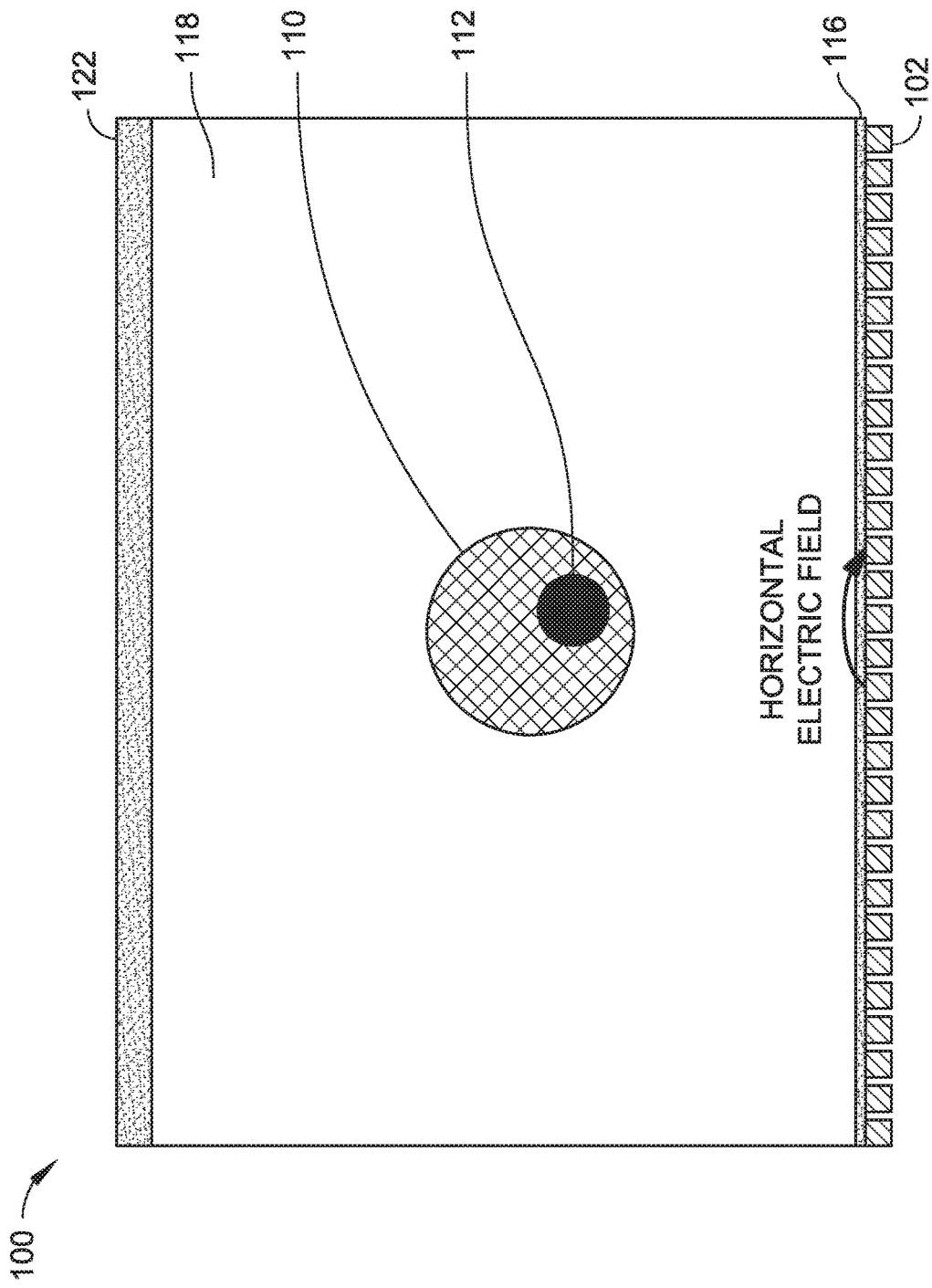
FIG. 4 is a schematic side view of an electric-field imager implemented in accordance with an embodiment of this disclosure, wherein the electric-field imager is configured to detect disturbances in a horizontal electric field.

In some embodiments, the electric-field imaging system 100 relies on a substantially vertical electric field. As shown in FIG. 3, for example, a driving electrode 120 can be located above the electric field sensor array defined by the metal panels 102. In some embodiments, the metal panels 102 are covered by an insulator 116 (e.g., glass or plastic substrate) that separates the metal panels 102 from the fluid 118 containing the target analytes (e.g., cells 110, cellular structures 112, etc.). The driving electrode 120 can induce a vertical electric field that is formed between the driving electrode 120 and the sensor array of metal panels 102 disposed below. The electric-field imaging system 100 can additionally or alternatively rely on a substantially horizontal electric field. For example, as shown in FIG. 4, a single pixel/panel 102, line of pixels/panels 102, or one or more regions of pixels/panels 102 can be driven, and the rest of the pixels/panels 102 in the electric field image sensor array can detect the electric field generated by the pixels/panels being driven. The presence of analytes like microparticles, viruses, cells, in the fluid disturbs the electric field (e.g., changes in impedance or charge detected from driving pixel/panel 102 to receiving pixel/panel).

In some embodiments, the driving electrode 120 or an insulator 122 (e.g., glass or plastic substrate) is positioned over the fluid sample, such that the fluid sample is sandwiched between the active sensor array and the electrode 120 or insulator 122. Positioning of the electrode 120 or insulator 122 can be used to limit the possible distance between target analytes in the fluid and the metal panels 102 of the sensor array. In some embodiments, the distance is limited to approximately 10 microns or less.

Example Processes

Figure 5:
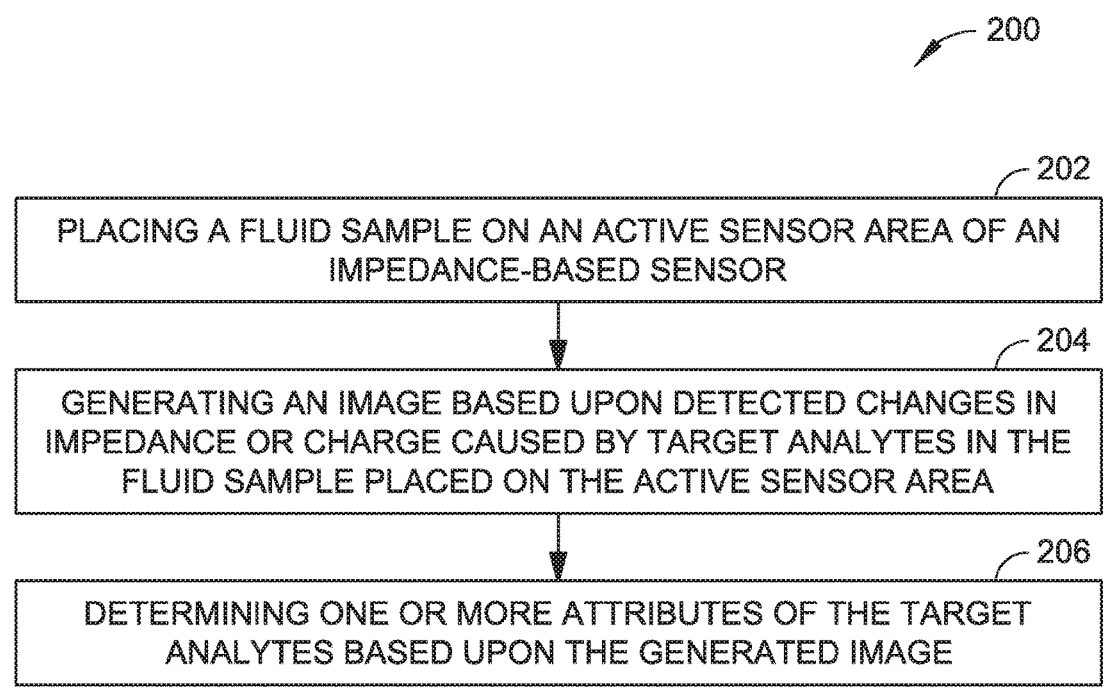
FIG. 5 is flow diagram illustrating a method of imaging microparticles, viruses, cells or beads in a fluid sample with an impedance based sensor, such as the electric field imager illustrated in FIGS. 1 through 4 in accordance with various embodiments of this disclosure.

FIG. 5 shows a flow diagram for a method 200 of imaging target analytes with an electric-field imaging system, such as the system 100 described herein. Accordingly, the method 200 may include any steps or operations that are described herein with regard to the electric-field imaging system 100 or that are necessary for achieving an attribute of the electric-field imaging system 100 that is described herein. However, the method 200 is in no way limited to any embodiment of the electric-field imaging system 100 described herein.

As shown in FIG. 5, the method 200 can include: (202) placing a fluid sample (e.g., blood sample or other biological sample) on an active sensor area of an impedance-based sensor (e.g., system 100), the fluid sample containing target analytes (e.g., biological microparticles, viruses, cells, beads, or the like); (204) generating an image based upon changes in impedance or charge caused by the target analytes in the fluid placed on the active sensor area; and (206) determining one or more attributes of the target analytes based upon the generated image. In some implementations, determining the one or more attributes of the target analytes based upon the generated image (step 206) can include performing of a comparison between one or more portions of the generated image with a library of stored images or data structures. For example, computer imaging algorithms may be executed by one or more processors to perform comparisons with a library of stored images or parameters to determine attributes of the microparticles, viruses, cells, or beads including one or more of: size, type, morphology, volume, distribution, number, concentration, or motility of the target analytes.

In some implementations, the impedance-based sensor can include multiple active sensor areas or regions (e.g., as discussed above with regard to system 100) with different respective sensor pitches suitable for detecting differently sized particles (or different ranges of particles sizes). The method can further include as step of selecting a first sensor area or a second sensor area based upon a size of the target analyte being imaged.

In some implementations, the method can further include generating a second image based upon changes in impedance or charge caused by the target analytes in the fluid placed on the active sensor area, the second image being generated at a second later point in time relative to the first image. For example, time lapsed images can be used to monitor cells as they multiply or for agglutination assaying to monitor movement of dispersed particles (e.g., antibody-coated microbeads 114 shown in FIG. 2A) as they agglutinate in the presence of an antigen (e.g., as shown in FIG. 2B).

Those skilled in the art will appreciate that the forgoing steps or operations can be carried out in any order, unless otherwise indicated herein, and that one or more steps may be carried out substantially simultaneously or at least partially in parallel. It should be further recognized that the various functions, operations, blocks, or steps described throughout the present disclosure may be carried out by any combination of hardware, software, or firmware. Various steps or operations may be carried out by one or more of the following: electronic circuitry, logic gates, multiplexers, a programmable logic device, an application-specific integrated circuit (ASIC), a controller/microcontroller, or a computing system. A computing system may include, but is not limited to, a personal computing system, mainframe computing system, workstation, image computer, parallel processor, or any other device known in the art. In general, the terms "controller" and "computing system" are broadly defined to encompass any device having one or more processors, which execute instructions from a carrier medium.

Program instructions implementing methods, such as those manifested by embodiments described herein, may be transmitted over or stored on carrier medium. The carrier medium may be a transmission medium, such as, but not limited to, a wire, cable, or wireless transmission link. The carrier medium may also include a non-transitory signal bearing medium or storage medium such as, but not limited to, a read-only memory, a random access memory, a magnetic or optical disk, a solid-state or flash memory device, or a magnetic tape.

It is further contemplated that any embodiment of the disclosure manifested above as a system or method may include at least a portion of any other embodiment described herein. Those having skill in the art will appreciate that there are various embodiments by which systems and methods described herein can be implemented, and that the implementation will vary with the context in which an embodiment of the disclosure is deployed.

Furthermore, it is to be understood that the invention is defined appended claims. Although embodiments of this invention have been illustrated, it is apparent that various modifications may be made by those skilled in the art without departing from the scope and spirit of the disclosure.

What is claimed is:

1. An electric-field imaging system, comprising:
   an impedance-based sensor having an active sensor area with a sensor pitch that is higher frequency than a Nyquist spatial sampling rate suitable for detecting a smallest member of a group of one or more target analytes in a fluid sample; and
   a driving electrode positioned relative to the active sensor area, the driving electrode being configured to generate an electric field, wherein the active sensor area is configured to detect the electric field.

2. The electric-field imaging system of claim 1, further comprising:
   a processor configured to receive imaging data associated with a change in impedance or charge detected by the impedance-based sensor when the fluid sample is placed on the active sensor area, the processor being further configured to determine one or more attributes of the one or more target analytes based upon the imaging data.

3. The electric-field imaging system of claim 2, wherein the imaging data includes multiple image frames collected at different times.

4. The electric-field imaging system of claim 2, wherein the one or more attributes determined by the processor include one or more of: size, type, morphology, volume, distribution, number, concentration, or motility of the one or more target analytes.

5. The electric-field imaging system of claim 2, wherein the processor is configured to determine the one or more attributes of the one or more target analytes at least in part by comparing the imaging data with a library of stored images or data structures.

6. The electric-field imaging system of claim 1, wherein the active sensor area comprises:
a plurality of metal panels configured to detect a change in impedance or charge due to proximity of the one or more target analytes in the fluid sample with respect to at least one metal panel of the plurality of metal panels.

7. The electric-field imaging system of claim 6, wherein at least a first metal panel is configured to generate a substantially horizontal electric field relative to the plurality of metal panels, and at least a second metal panel is configured to detect the substantially horizontal electric field.

8. The electric-field imaging system of claim 7, wherein the plurality of metal panels are configured to be selectively driven, individually or in groups, by transmitter circuitry to generate the substantially horizontal electric field.

9. The electric-field imaging system of claim 1, further comprising:
a first insulator positioned over the active sensor area, the first insulator being configured to prevent the fluid sample from directly contacting sensor elements of the active sensor area.

10. The electric-field imaging system of claim 1, further comprising:
a second insulator positioned a distance above the active sensor area, wherein a distance between the one or more target analytes in the fluid sample and the active sensor area is limited by the second insulator.

11. The electric-field imaging system of claim 1, wherein the impedance-based sensor further comprises a second active sensor area with a second sensor pitch suitable for detecting differently sized particles from the one or more target analytes detectable by the first active sensor area.

12. The electric-field imaging system of claim 1, further comprising at least one of a thermal sensor configured to measure a temperature of the fluid sample or a conductivity sensor configured to measure a conductivity of the fluid sample.

13. The electric field imaging system of claim 1, wherein the impedance-based sensor is further configured to measure a conductivity of the fluid sample.

\* \* \* \* \*